(12) United States Patent
Su et al.

(10) Patent No.: US 11,859,777 B2
(45) Date of Patent: Jan. 2, 2024

(54) LIGHT BULB APPARATUS

(71) Applicant: XIAMEN LEEDARSON LIGHTING CO., LTD, Fujian (CN)

(72) Inventors: Mingnan Su, Fujian (CN); Guangai Chen, Fujian (CN); Chunhua Wang, Fujian (CN); Shenghong Liu, Fujian (CN)

(73) Assignee: XIAMEN LEEDARSON LIGHTING CO., LTD, Fujian (CN)

( * ) Notice: Subject to any disclaimer, the term of this patent is extended or adjusted under 35 U.S.C. 154(b) by 0 days.

(21) Appl. No.: 17/117,798

(22) Filed: Dec. 10, 2020

(65) Prior Publication Data
US 2021/0172571 A1 Jun. 10, 2021

(30) Foreign Application Priority Data
Dec. 10, 2019 (CN) .......................... 201922196284.7

(51) Int. Cl.
| | |
|---|---|
| F21K 9/238 | (2016.01) |
| F21K 9/232 | (2016.01) |
| F21K 9/237 | (2016.01) |
| F21V 17/10 | (2006.01) |
| F21V 23/04 | (2006.01) |
| A61L 2/10 | (2006.01) |
| A61L 2/24 | (2006.01) |
| F21V 5/04 | (2006.01) |
| F21Y 115/10 | (2016.01) |

(52) U.S. Cl.
CPC ............... *F21K 9/238* (2016.08); *A61L 2/10* (2013.01); *A61L 2/24* (2013.01); *F21K 9/232* (2016.08); *F21K 9/237* (2016.08); *F21V 5/045* (2013.01); *F21V 17/101* (2013.01); *F21V 23/0471* (2013.01); *A61L 2202/11* (2013.01); *A61L 2202/14* (2013.01); *F21Y 2115/10* (2016.08)

(58) Field of Classification Search
CPC .......... F21K 9/238; F21K 9/232; F21K 9/237; A61L 2/10; A61L 2/24; F21V 5/045; F21V 17/101; F21V 23/0471
See application file for complete search history.

(56) References Cited

U.S. PATENT DOCUMENTS

| | | | | |
|---|---|---|---|---|
| 2007/0109763 | A1* | 5/2007 | Wolf | F21V 19/006 362/86 |
| 2010/0277067 | A1* | 11/2010 | Maxik | F21K 9/23 315/32 |
| 2011/0068687 | A1* | 3/2011 | Takahasi | F21V 23/009 315/35 |
| 2011/0074289 | A1* | 3/2011 | Van de Ven | F21K 9/233 315/32 |

(Continued)

*Primary Examiner* — Christopher E Dunay
(74) *Attorney, Agent, or Firm* — Chun-Ming Shih; LANWAY IPR SERVICES

(57) ABSTRACT

A light bulb apparatus includes a glass housing, a sleeve housing, a light source plate, a sleeve connector wrapping and an Edison cap. The glass housing defines a tubular part and a trumpet part. The sleeve housing includes a neck part and a protruding part. The neck part is enclosed by the tubular part of the glass housing. The protruding part is exposed outside tubular part. The light source plate is fixed to the sleeve housing. The sleeve connector wraps an exterior surface of the protruding part. The Edison cap is attached to the sleeve connector.

19 Claims, 7 Drawing Sheets

(56) References Cited

U.S. PATENT DOCUMENTS

| | | | | |
|---|---|---|---|---|
| 2012/0058663 | A1* | 3/2012 | Oster | F21K 9/23 |
| | | | | 439/339 |
| 2013/0162139 | A1* | 6/2013 | Liu | F21V 13/02 |
| | | | | 315/51 |
| 2013/0265760 | A1* | 10/2013 | Demuynck | F21K 9/23 |
| | | | | 362/240 |
| 2014/0063809 | A1* | 3/2014 | Huang | F21V 29/773 |
| | | | | 362/294 |
| 2014/0211497 | A1* | 7/2014 | Yuan | F21K 9/233 |
| | | | | 362/555 |
| 2015/0062893 | A1* | 3/2015 | Lynn | A61L 2/10 |
| | | | | 362/231 |

* cited by examiner

LIGHT BULB APPARATUS

FIELD

The present invention is related to a light bulb apparatus, and more particularly related to a light bulb apparatus with a housing with multiple materials.

BACKGROUND

The time when the darkness is being lighten up by the light, human have noticed the need of lighting up this planet. Light has become one of the necessities we live with through the day and the night. During the darkness after sunset, there is no natural light, and human have been finding ways to light up the darkness with artificial light. From a torch, candles to the light we have nowadays, the use of light have been changed through decades and the development of lighting continues on.

Early human found the control of fire which is a turning point of the human history. Fire provides light to bright up the darkness that have allowed human activities to continue into the darker and colder hour of the hour after sunset. Fire gives human beings the first form of light and heat to cook food, make tools, have heat to live through cold winter and lighting to see in the dark.

Lighting is now not to be limited just for providing the light we need, but it is also for setting up the mood and atmosphere being created for an area. Proper lighting for an area needs a good combination of daylight conditions and artificial lights. There are many ways to improve lighting in a better cost and energy saving. LED lighting, a solid-state lamp that uses light-emitting diodes as the source of light, is a solution when it comes to energy-efficient lighting. LED lighting provides lower cost, energy saving and longer life span.

The major use of the light emitting diodes is for illumination. The light emitting diodes is recently used in light bulb, light strip or light tube for a longer lifetime and a lower energy consumption of the light. The light emitting diodes shows a new type of illumination which brings more convenience to our lives. Nowadays, light emitting diode light may be often seen in the market with various forms and affordable prices.

After the invention of LEDs, the neon indicator and incandescent lamps are gradually replaced. However, the cost of initial commercial LEDs was extremely high, making them rare to be applied for practical use. Also, LEDs only illuminated red light at early stage. The brightness of the light only could be used as indicator for it was too dark to illuminate an area. Unlike modern LEDs which are bound in transparent plastic cases, LEDs in early stage were packed in metal cases.

In 1878, Thomas Edison tried to make a usable light bulb after experimenting different materials. In November 1879, Edison filed a patent for an electric lamp with a carbon filament and keep testing to find the perfect filament for his light bulb. The highest melting point of any chemical element, tungsten, was known by Edison to be an excellent material for light bulb filaments, but the machinery needed to produce super-fine tungsten wire was not available in the late 19th century. Tungsten is still the primary material used in incandescent bulb filaments today.

Early candles were made in China in about 200 BC from whale fat and rice paper wick. They were made from other materials through time, like tallow, spermaceti, colza oil and beeswax until the discovery of paraffin wax which made production of candles cheap and affordable to everyone. Wick was also improved over time that made from paper, cotton, hemp and flax with different times and ways of burning. Although not a major light source now, candles are still here as decorative items and a light source in emergency situations. They are used for celebrations such as birthdays, religious rituals, for making atmosphere and as a decor.

Illumination has been improved throughout the times. Even now, the lighting device we used today are still being improved. From the illumination of the sun to the time when human can control fire for providing illumination which changed human history, we have been improving the lighting source for a better efficiency and sense. From the invention of candle, gas lamp, electric carbon arc lamp, kerosene lamp, light bulb, fluorescent lamp to LED lamp, the improvement of illumination shows the necessity of light in human lives.

There are various types of lighting apparatuses. When cost and light efficiency of LED have shown great effect compared with traditional lighting devices, people look for even better light output. It is important to recognize factors that can bring more satisfaction and light quality and flexibility.

A PR light bulb is a type of light bulb frequently used in commercial places. It is difficult in the past to assemble a PR light bulb.

Therefore, it is beneficial if a better design is provided for conveniently assembling a PR light bulb or other light bulbs with several different materials.

SUMMARY

In some embodiments, a light bulb apparatus includes a glass housing, a sleeve housing, a light source plate, a sleeve connector and an Edison cap.

The glass housing defines a tubular part and a trumpet part.

The sleeve housing includes a neck part and a protruding part.

The neck part is enclosed by the tubular part of the glass housing.

The protruding part is exposed outside tubular part.

The light source plate is fixed to the sleeve housing.

The sleeve connector wraps an exterior surface of the protruding part.

The Edison cap is attached to the sleeve connector.

In some embodiments, the sleeve housing has a sleeve trumpet extended from the neck part toward the trumpet part of the glass housing.

The sleeve trumpet prevents the sleeve housing moving downwardly when the sleeve trumpet engages the trumpet part of the glass housing.

In some embodiments, the sleeve trumpet has a reflective layer in an inner surface for reflecting a light of the light source plate.

In some embodiments, the sleeve connector has a screw groove on an exterior surface of the sleeve connector for fixing the Edison cap by rotation.

In some embodiments, the sleeve connector is fixed to the Edison cap with a rivet.

In some embodiments, the sleeve connector has a screw groove on an interior surface of the sleeve connector for fixing the protruding part by rotation.

In some embodiments, the glass housing has a concave stop structure for preventing the sleeve housing moving downwardly when the neck part of the sleeve housing engages the concave stop structure.

In some embodiments, the sleeve housing has a gap opening for adjustment during thermal expansion and contraction.

In some embodiments, a driver is disposed inside the sleeve housing.

In some embodiments, the driver has a driver plate mounted with driver circuits.

The driver plate is inserted to the sleeve housing along a sliding track of the sleeve housing.

In some embodiments, a lens is standing upon the light source plate.

In some embodiments, there are multiple concentric circles with different height levels disposed on an top surface of the lens.

In some embodiments, a light passing cover covers the lens.

In some embodiments, a driver component is placed on the light source plate outside covering of the lens.

In some embodiments, a glue layer is disposed between the glass housing and the sleeve housing.

In some embodiments, the glue layer is heat dissipation glue.

In some embodiments, the sleeve connector is manually rotatable for changing a setting of LED modules on the light source plate.

In some embodiments, there is a manual switch for changing a setting of LED modules on the light source plate.

In some embodiments, an ultra-violet light source and a motion sensor is disposed on the light source plate.

When the motion sensor indicates no person is nearby, the ultra-violet light source emits ultra-violet light to perform sterilization.

In some embodiments, the ultra-violet light is turn off after a predetermined time period.

DETAILED DESCRIPTION

Figure 6:
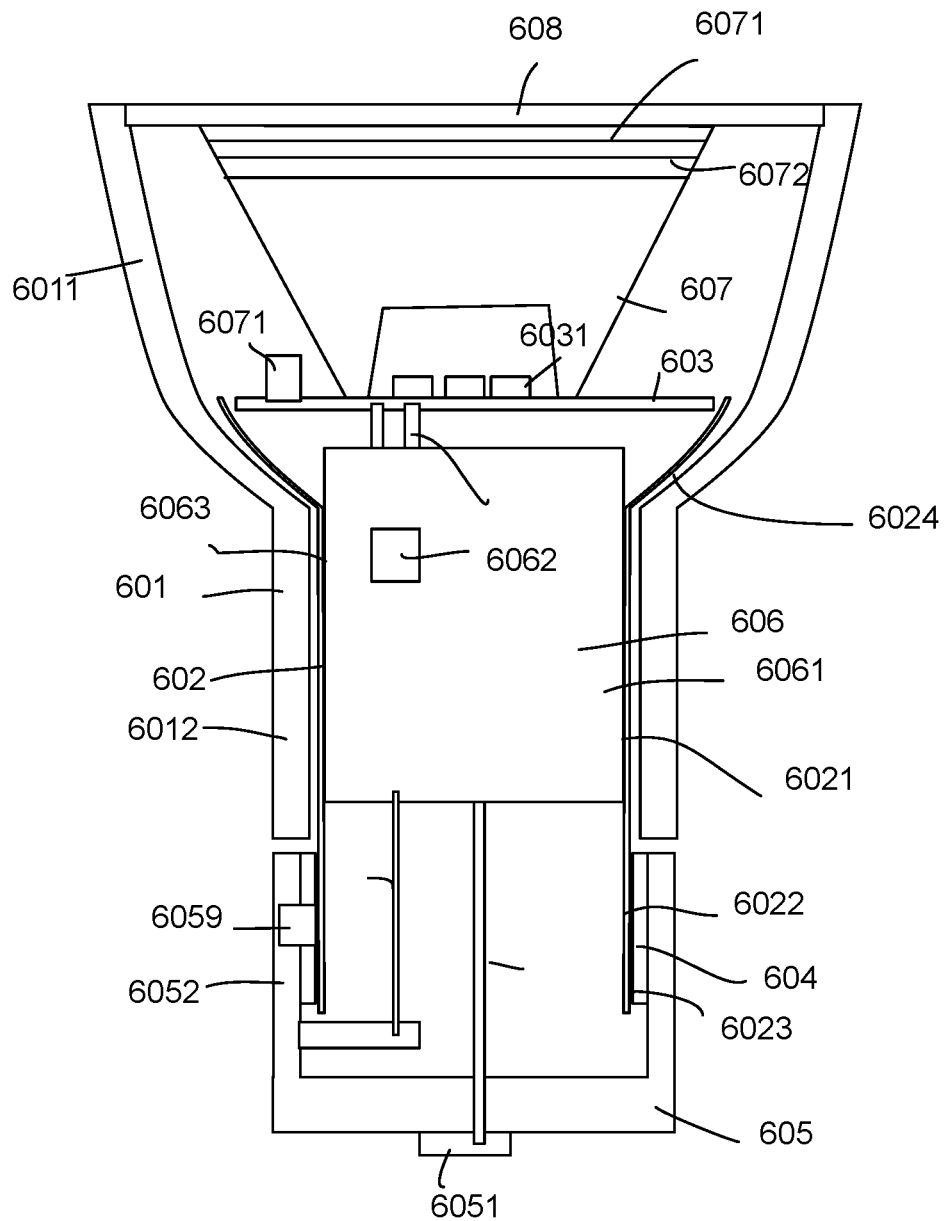
FIG. 6 shows another embodiment of a light bulb apparatus.

Please refer to FIG. 6, a light bulb apparatus includes a glass housing 601, a sleeve housing 602, a light source plate 603, a sleeve connector 604 and an Edison cap 605.

The Edison cap 605 has various standards and is used in daily life to screw a light bulb to an Edison socket to receive power supply.

The glass housing 601 defines a tubular part 6012 and a trumpet part 6011. The trumpet part 6011 has an enlarging profile extended from a top end of the tubular part 6012. The tubular part 6012 has a tube shape, leaving an inner space empty for inserting a portion of the sleeve housing 602.

The sleeve housing 602 includes a neck part 6021 and a protruding part 6022.

The neck part 6021 is enclosed by the tubular part 6012 of the glass housing 601.

The protruding part 6022 is exposed outside tubular part 6012 of the glass housing 601.

The light source plate 603 is fixed to the sleeve housing 602, e.g. on top of the sleeve housing 602. The glass housing 601 is made of glass material. The sleeve housing 602 may be made of plastic, metal material or complex material mixed with multiple materials.

The sleeve connector 604 wraps an exterior surface 6023 of the protruding part 6022.

The Edison cap 605 is attached to the sleeve connector 604. The Edison cap 605 has two electrodes 6051, 6052 connecting to two ends of an electrical wire via an Edison socket. The two electrodes 6051, 6052 are respectively connected to a driver 606. The driver 606 includes a driver plate 6061 and a driver circuit 6062.

The light bulb apparatus has a glass appearing while being easy to be assembled.

In some embodiments, the sleeve housing 602 has a sleeve trumpet 6024 extended from the neck part 6021 toward the trumpet part 6011 of the glass housing 601.

The sleeve trumpet 6024 prevents the sleeve housing 602 moving downwardly when the sleeve trumpet 6024 engages the trumpet part 6011 of the glass housing 601.

Specifically, the sleeve trumpet has a larger diameter than the diameter of the tubular part 6012 of the glass housing 601 and thus stops the sleeve housing 602 to keep moving downwardly when the sleeve trumpet 6024 engages the trumpet part 6011.

On the other end of the sleeve housing 602, the protruding part 6022 is further fixed with a sleeve connector 604 and thus the sleeve housing 602 is kept at its position relative to the glass housing easily and conveniently.

Figure 7:
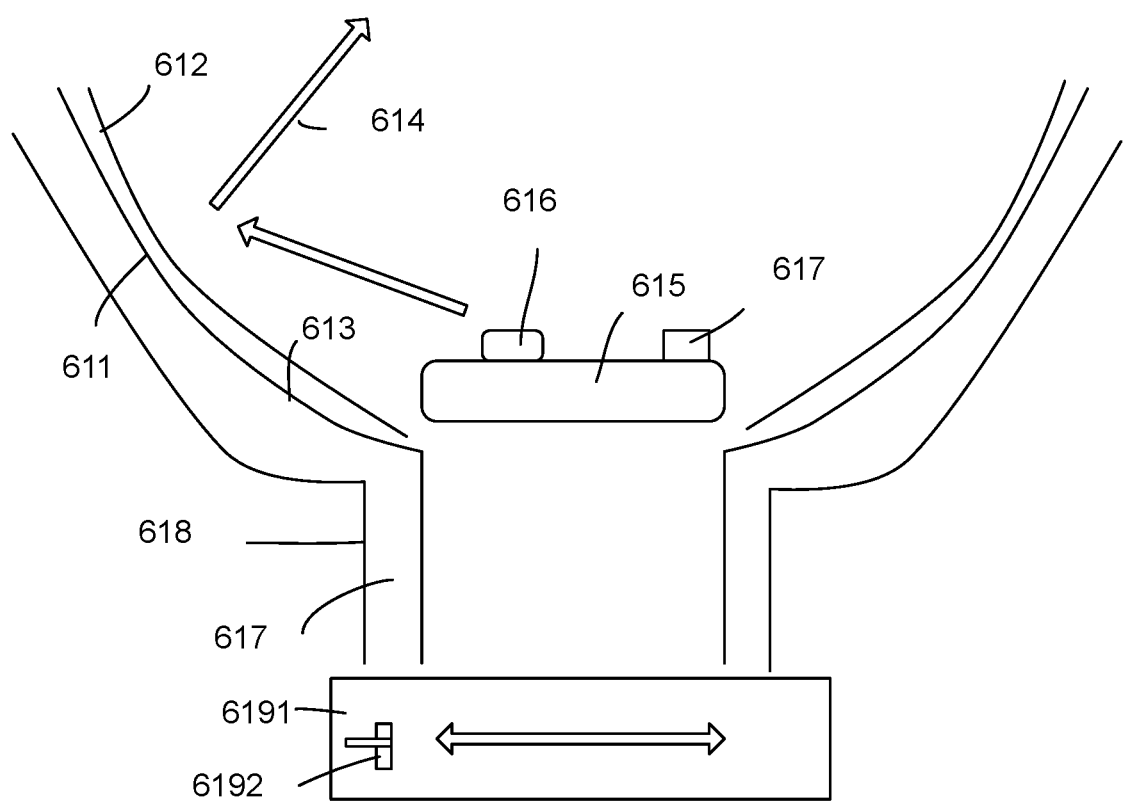
FIG. 7 shows another embodiment of a light bulb apparatus.

In FIG. 7, the sleeve trumpet 611 has a reflective layer 612 in an inner surface 613 for reflecting a light 614 of the light source plate 615.

Figure 8:
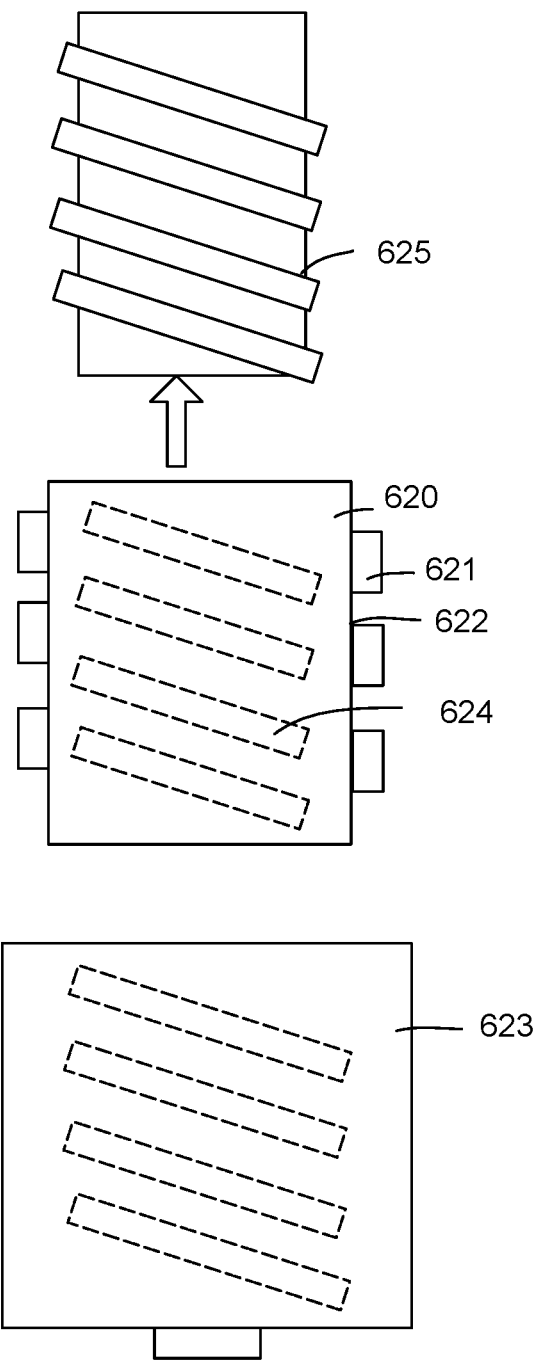
FIG. 8 shows an example for assembling multiple components.

In FIG. 8, the sleeve connector 620 has a screw groove 621 on an exterior surface 622 of the sleeve connector 620 for fixing the Edison cap 623 by rotation.

In FIG. 6, the sleeve connector 604 may be fixed to the Edison cap 605 with a rivet 6057.

In FIG. 8, the sleeve connector 620 has a screw groove 624 on an interior surface of the sleeve connector 620 for fixing the protruding part 625 by rotation.

Figure 2:
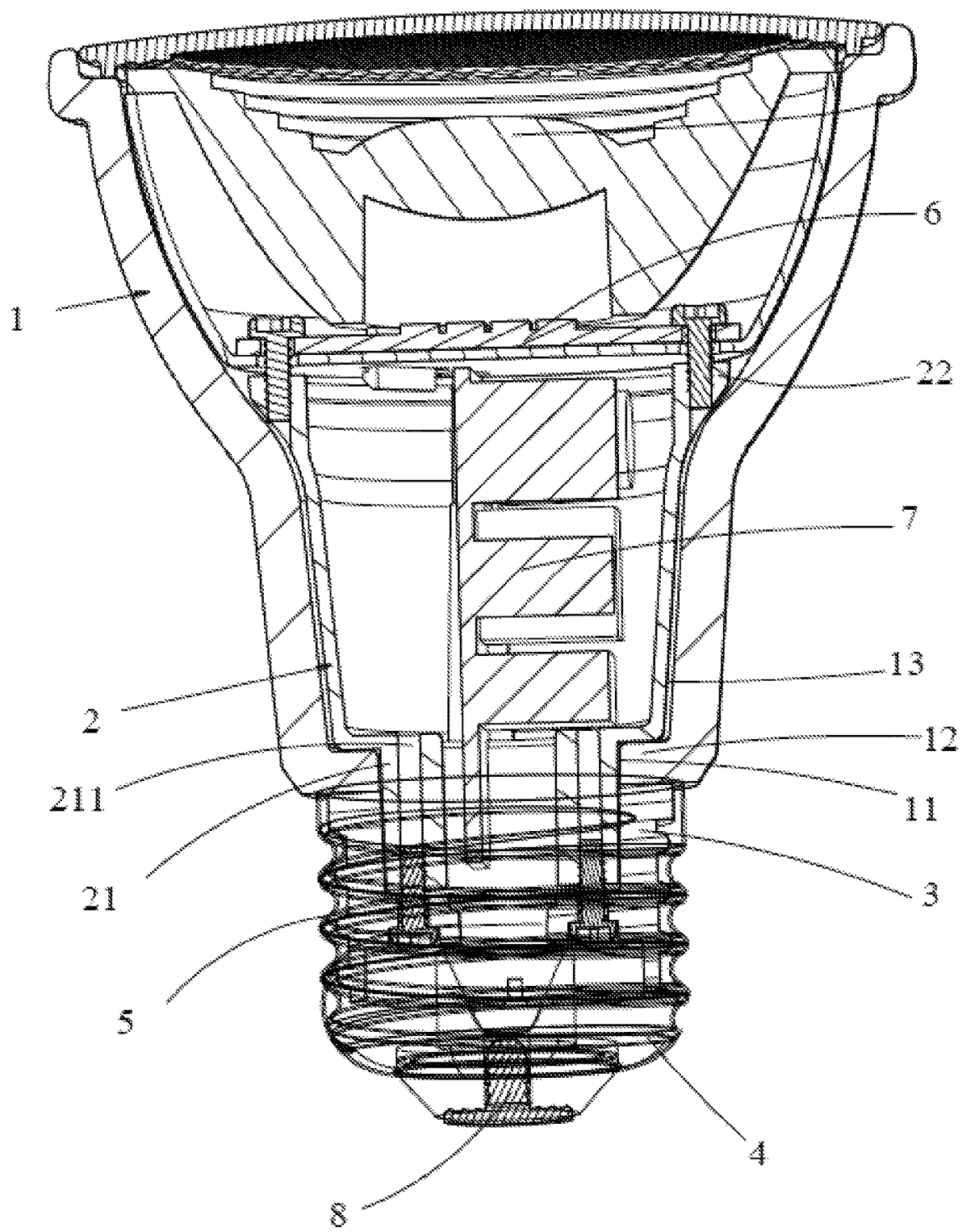
FIG. 2 illustrates a cross-sectional view of the embodiment of FIG. 1.

In FIG. 2, the glass housing has a concave stop structure 12 for preventing the sleeve housing 2 moving downwardly when the neck part of the sleeve housing 2 engages the concave stop structure 12.

Figure 4:
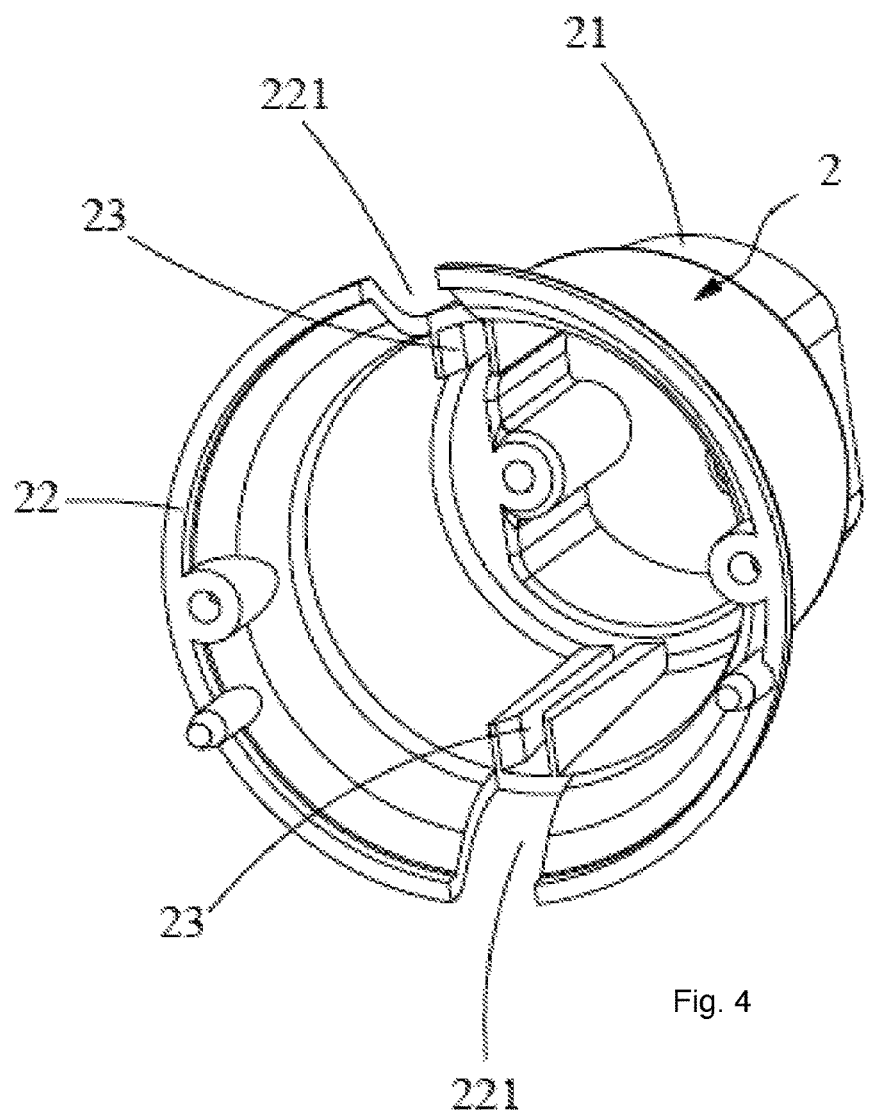
FIG. 4 illustrates a sleeve housing example.

In FIG. 4, the sleeve housing has a gap opening 221 for adjustment during thermal expansion and contraction. Specifically, the glass housing and the sleeve housing have different thermal expansion ratios. Thus, the gap opening 221 provides an elastic space preventing damage of the components during thermal expansion and contraction.

In FIG. 6, a driver 606 is disposed inside the sleeve housing 602.

In some embodiments, the driver 606 has a driver plate 6061 mounted with driver circuits 6062.

The driver plate 6061 is inserted to the sleeve housing 602 along a sliding track 6063 of the sleeve housing 602.

In FIG. 6, a lens 607 is standing upon the light source plate 603.

In some embodiments, there are multiple concentric circles 6071, 6072 with different height levels disposed on a top surface of the lens 607.

Such lens 607 may be a condensing lens or a diffusion lens depending on design requirement.

In some embodiments, a light passing cover 608 covers the lens 607.

In some embodiments, a driver component 6071 is placed on the light source plate 603 outside covering of the lens 607. Such design prevents the driver component 6071 making shadow or affecting light output of the light source plate 603, when LED modules 6031 are placed at center area of the light source plate 603 covered by the lens 607.

In FIG. 7, a glue layer 617 is disposed between the glass housing 618 and the sleeve housing 611.

In some embodiments, the glue layer is heat dissipation glue for performing heat dissipation.

In FIG. 7, the sleeve connector 6191 is manually rotatable with respect to the sleeve housing for changing a setting of LED modules on the light source plate 615.

For example, the sleeve connector 6191 is exposed and placed below the glass housing but before the Edison cap. The sleeve connector 6191 is designed to be rotatable with respect to the glass housing and triggers a mechanic switch connected to a driver to change a setting of the LED modules, e.g. to change to different color temperatures.

In some embodiments, there is a manual switch 6192 for changing a setting of LED modules on the light source plate 615.

In some embodiments, an ultra-violet light source 616 and a motion sensor 617 is disposed on the light source plate 615.

When the motion sensor indicates no person is nearby, the ultra-violet light source emits ultra-violet light to perform sterilization.

In some embodiments, the ultra-violet light is turn off after a predetermined time period, e.g. to turn off sterilization after 30 minutes.

Figure 1:
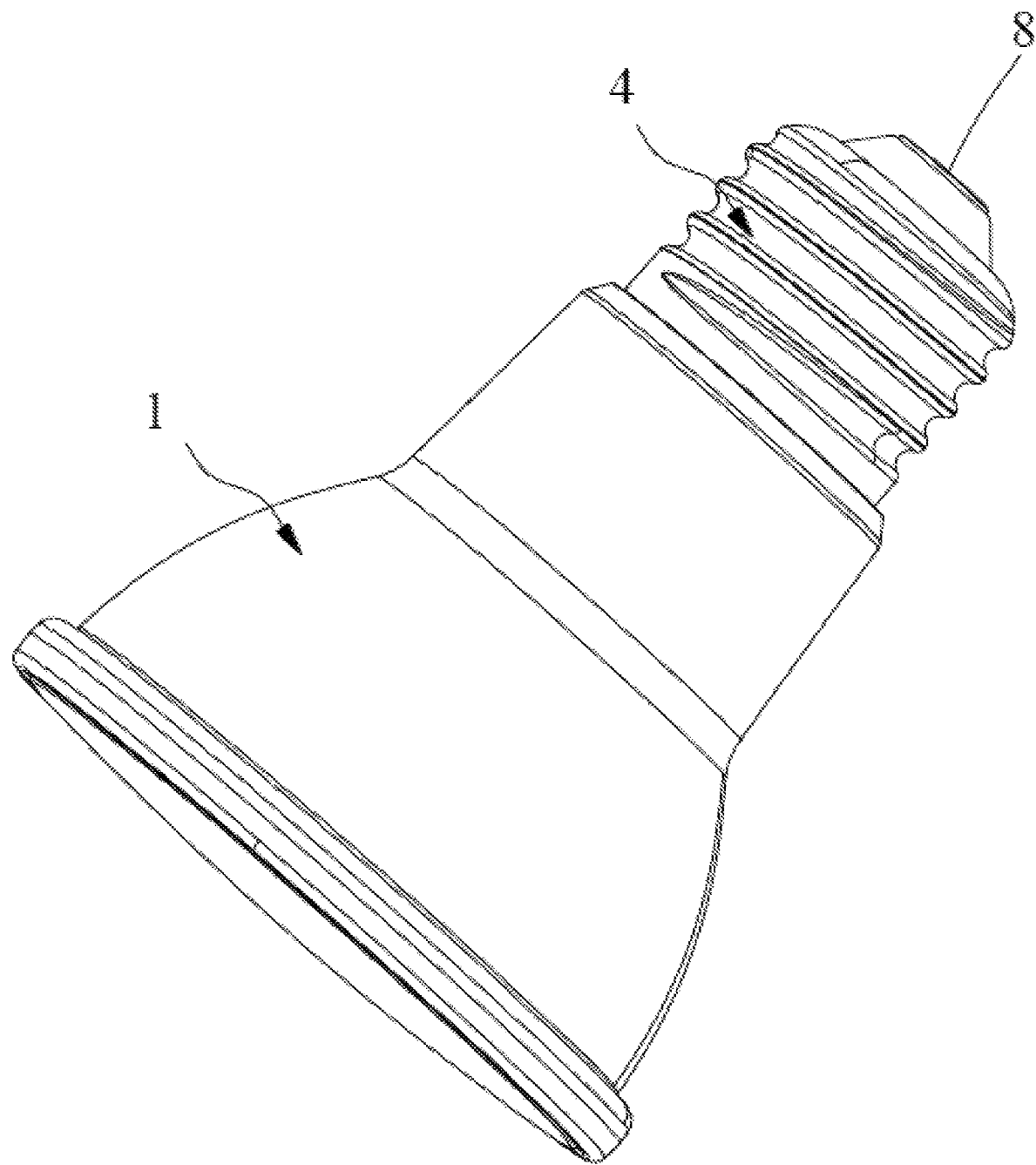
FIG. 1 illustrates an embodiment of a light bulb apparatus embodiment.

Please refer to FIG. 1, which shows a light bulb apparatus embodiment.

In FIG. 1, the light bulb apparatus has a Edison cap 4 and a glass housing 1. The Edison cap has an electrode 8 at its bottom.

Please refer to FIG. 2, which shows a cross-sectional view of the example in FIG. 1.

In FIG. 2, a light source plate 6 is placed on a sleeve housing 2. The sleeve housing 2 is enclosed by the glass housing 1 by inserting into a container hole 13. There is a concave stop structure 12. There is a driver 7 for rectifying input power and generates a driving current. There is a sleeve connector 21 connected to the protruding part 211 of the sleeve housing 2. There is an escape hole. The Edison cap 4 has a screw head 6 and a bottom electrode 8. An exterior surface of the sleeve connector has screw grooves 3.

Figure 3:
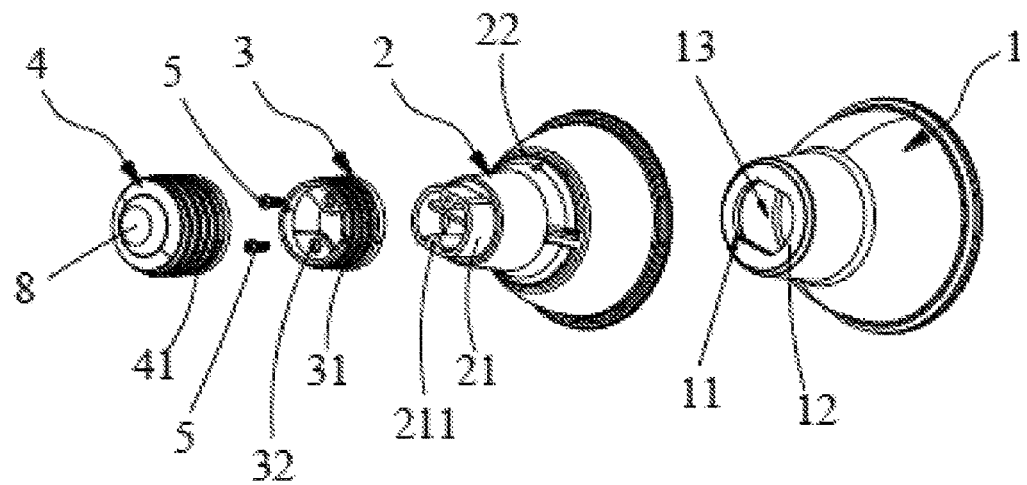
FIG. 3 illustrates an exploded view of a light bulb apparatus.

FIG. 3 shows an exploded view of the example in FIG. 1.

The glass housing has a container hole 13, a concave stop structure 12, and an escape hole 11. The sleeve housing 2 has a sleeve trumpet 22 and a protruding part 21. There is a screw groove 211 for installing the sleeve connector 3. The sleeve connector 3 has a screw groove 31. There is a connecting hole 32. Rivets 5 are used for fixing components.

The Edison cap 4 has an inner screw groove 41 and a bottom electrode 8.

Please refer to FIG. 4, which illustrates an example of the sleeve housing 2. There are a protruding part 21, a gap opening 221 for preventing damages during thermal expansion and retraction, a sliding track 23 for inserting a driver plate as mentioned above, and a sleeve trumpet 22.

Figure 5:
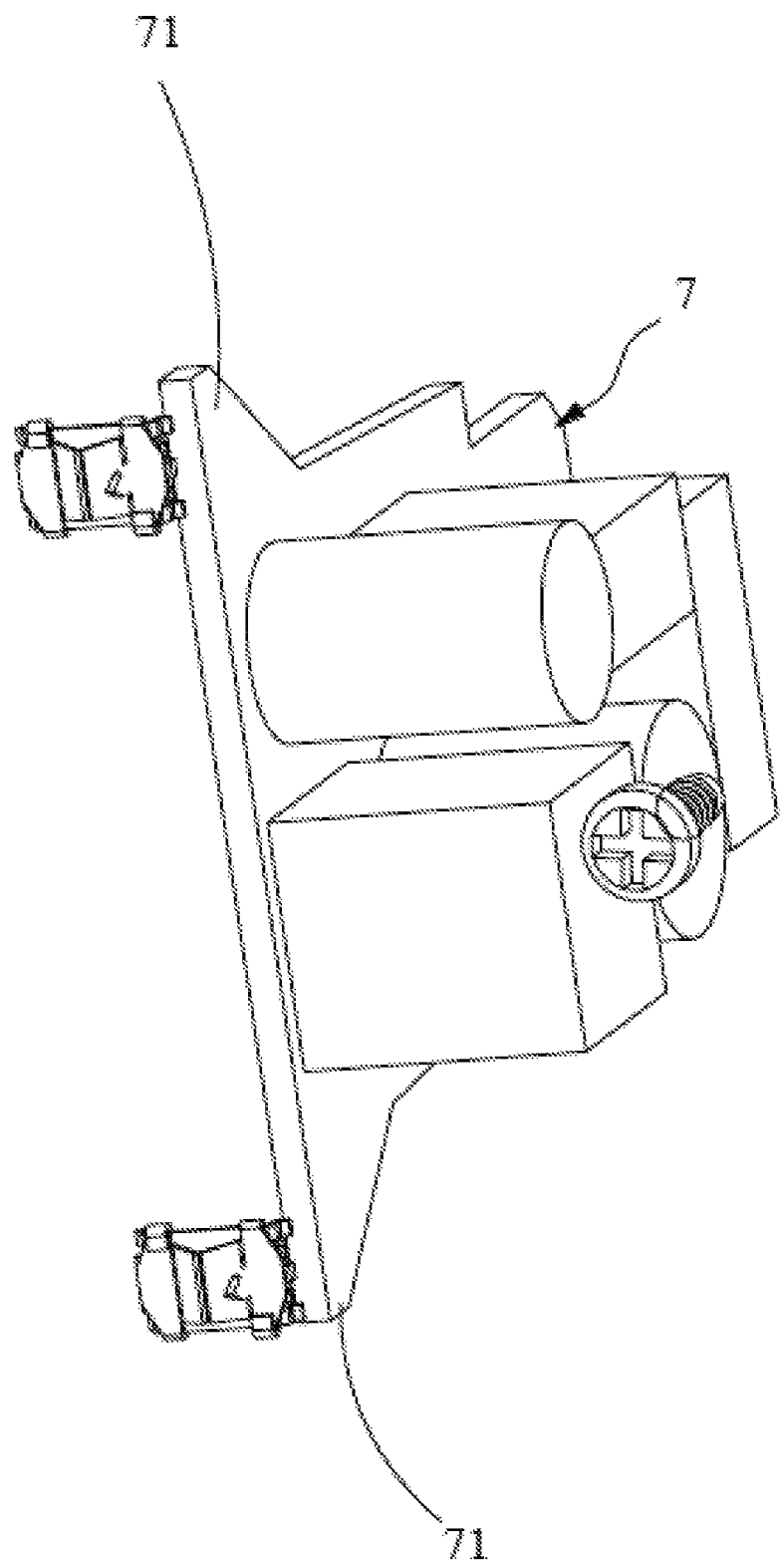
FIG. 5 illustrates a driver example.

Please refer to FIG. 5. In FIG. 5, a driver 7 is illustrated to have a driver plate 71 to be inserted into the sleeve housing in FIG. 4.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings.

The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

The invention claimed is:

1. A light bulb apparatus, comprising:
a glass housing defining a tubular part and a trumpet part;
a sleeve housing comprising a neck part and a protruding part, wherein the neck part is enclosed by the tubular part of the glass housing, the protruding part is exposed outside tubular part, and the protruding part is enlarged from the neck part along a part of the trumpet part;
a light source plate fixed to the sleeve housing;
a sleeve connector wrapping an exterior surface of the protruding part;
a light passing cover that is a flat plate and an edge of the light passing cover is aligned with an edge of the trumpet part, wherein the trumpet part has an enlarging profile extended from a top end of the tubular part to the edge of the light passing cover; and
an Edison cap attached to the sleeve connector, wherein the sleeve connector is manually rotatable for changing a setting of LED modules on the light source plate.

2. The light bulb apparatus of claim 1, wherein the sleeve housing has a sleeve trumpet extended from the neck part toward the trumpet part of the glass housing, the sleeve trumpet prevents the sleeve housing moving downwardly when the sleeve trumpet engages the trumpet part of the glass housing.

3. The light bulb apparatus of claim 2, wherein the sleeve trumpet has a reflective layer in an inner surface for reflecting a light of the light source plate.

4. The light bulb apparatus of claim 1, wherein the sleeve connector has a screw groove on an exterior surface of the sleeve connector for fixing the Edison cap by rotation.

5. The light bulb apparatus of claim 1, wherein the sleeve connector is fixed to the Edison cap with a rivet.

6. The light bulb apparatus of claim 1, wherein the sleeve connector has a screw groove on an interior surface of the sleeve connector for fixing the protruding part by rotation.

7. The light bulb apparatus of claim 1, wherein the glass housing has a concave stop structure for preventing the sleeve housing moving downwardly when the neck part of the sleeve housing engages the concave stop structure.

8. The light bulb apparatus of claim 1, wherein the sleeve housing has a gap opening for adjustment during thermal expansion and contraction.

9. The light bulb apparatus of claim 1, wherein a driver is disposed inside the sleeve housing.

10. The light bulb apparatus of claim 9, wherein the driver has a driver plate mounted with driver circuits, the driver plate is inserted to the sleeve housing along a sliding track of the sleeve housing.

11. The light bulb apparatus of claim 1, wherein a lens is standing upon the light source plate.

12. The light bulb apparatus of claim 11, wherein there are multiple concentric circles with different height levels disposed on a top surface of the lens.

13. The light bulb apparatus of claim 11, wherein the light passing cover covers the lens.

14. The light bulb apparatus of claim 11, wherein a driver component is placed on the light source plate outside covering of the lens.

15. The light bulb apparatus of claim 1, wherein a glue layer is disposed between the glass housing and the sleeve housing.

16. The light bulb apparatus of claim 15, wherein the glue layer is heat dissipation glue.

17. The light bulb apparatus of claim 1, wherein there is a manual switch for changing a setting of LED modules on the light source plate.

18. The light bulb apparatus of claim 1, wherein an ultra-violet light source and a motion sensor is disposed on the light source plate, when the motion sensor indicates no person is nearby, the ultra-violet light source emits ultra-violet light to perform sterilization.

19. The light bulb apparatus of claim 18, wherein the ultra-violet light is turn off after a predetermined time period.

* * * * *